United States Patent
Gjerde et al.

[11] Patent Number: 6,156,206
[45] Date of Patent: Dec. 5, 2000

[54] PROCESS FOR PERFORMING POLYNUCLEOTIDE SEPARATIONS

[75] Inventors: Douglas T. Gjerde, Saratoga; Robert M. Haefele, Palo Alto; David W. Togami, San Jose, all of Calif.

[73] Assignee: Transgenomic, Inc., San Jose, Calif.

[21] Appl. No.: 09/324,350

[22] Filed: Jun. 2, 1999

Related U.S. Application Data

[60] Division of application No. 09/081,039, May 18, 1998, Pat. No. 5,972,222, and a continuation-in-part of application No. 08/748,376, Nov. 13, 1996, Pat. No. 5,772,889.
[60] Provisional application No. 60/049,123, Jun. 10, 1997, and provisional application No. 60/063,835, Oct. 30, 1997.

[51] Int. Cl.[7] .................................................. B01D 15/08
[52] U.S. Cl. ....................... 210/635; 210/656; 210/659; 435/6; 536/25.4
[58] Field of Search ........................... 435/6; 536/23.1, 536/25.4; 210/635, 656, 659, 198.2

[56] References Cited

U.S. PATENT DOCUMENTS

| | | | |
|---|---|---|---|
| 4,563,510 | 1/1986 | Ugelstad | 562/66 |
| 4,683,202 | 7/1987 | Mullis | 435/91 |
| 4,855,225 | 8/1989 | Fung et al. | 435/6 |
| 5,205,929 | 4/1993 | Carr et al. | 210/198.2 |
| 5,207,914 | 5/1993 | Lin | 210/635 |
| 5,338,448 | 8/1994 | Gjerde | 210/198.2 |
| 5,453,185 | 9/1995 | Frechet et al. | 210/198.2 |
| 5,585,236 | 12/1996 | Bonn et al. | 435/5 |
| 5,616,701 | 4/1997 | Woodard et al. | 536/25.4 |
| 5,772,889 | 6/1998 | Gjerde et al. | 210/635 |
| 5,795,976 | 8/1998 | Oefner et al. | 536/25.4 |
| 5,843,312 | 12/1998 | Manz | 210/635 |

FOREIGN PATENT DOCUMENTS

| | | | |
|---|---|---|---|
| 0 507 591 A2 | 10/1992 | European Pat. Off. | 210/656 |
| 94/11305 | 5/1994 | WIPO | 210/656 |

OTHER PUBLICATIONS

Barder et al. Fast Chromatography and Nonporous Silica, LC–GC (1997) 15: 918–926, No. 10.

Chen et al. High–Speed High–Performance Liquid Chromatography of Peptides and Proteins, J. of Chromatography A (1995) 705: 3–20.

Huber et al, High–Resolution Liquid Chromatography of DNA Fragments on Non–Porous Poly9styrene–Divinylbenzene) Particles, Nucleic Acid Research, vol. 21 No. 5: 1061–1066 (1993).

Engelhardt et al. Polymer Encapsulated Stationary Phases: Advantages, Properties and Selectivities, Chromatographia (1989) 27: 535–543, No. 11/12.

Erikkson et al, Separation of DNA Restriction Fragments by Ion–Pair Chromatography, Journal of Chromatography, 359: 265–274 (1986).

(List continued on next page.)

*Primary Examiner*—Ernest G. Therkorn
*Attorney, Agent, or Firm*—William B. Walker

[57] ABSTRACT

The invention recognizes the deleterious effects of trace, and even undetectable amounts of multivalent cations on the separation of mixtures of polynucleotides, especially double stranded polynucleotides, and provides an improved method for separating such mixtures on wide pore, non-polar separation media by eliminating multivalent cations from the all aspects of the separation process. This is accomplished by using components in the separation process which are materials which do not release metal cations. In addition, the use of cation capture resins and other methods to remove residual traces of multivalent cations from eluting solvents, sample solutions, separation media, and system components is described. It is also important to remove any traces or organic contaminants from solvents solutions and system parts. Taking similar steps to remove residual traces of multivalent cations and organic impurities from the separation process, the invention may also be used in a batch process to separate mixtures of polynucleotide fragments.

17 Claims, 7 Drawing Sheets

OTHER PUBLICATIONS

Huber et al., Micropellicular Stationary Phases for High-Performance Liquid Chromatography of Double–Stranded DNA, J. of Chromatography A 806 (1998) pp. 1–28.

Iler et al. The Chemistry of Silica (1979) John Wiley & Sons, New York pp. 566–569.

Kalghatgi et al. Rapid Analysis of Proteins an Peptides by Reversed–Phase Chromatography, J. of Chromatography (1987) 398:335–339.

Nahum et al. Surface Silnols in Silica–Bonded Huydrocarbonaceous Stationary Phases, J. of Chromatography (1981) 203: 53–63.

Poole et al. Chromatography Today (1991) Elsevier, New York, pp. 313–342.

Schoburg et al. Immobilization of Stationary Liquids in Reversed– and Normal–Phase Liquid Chromatography, J. of Chromatography (1983) 282: 27–39.

Schoburg et al. Immobilization of Stationary Liquids of Silica Particles by Y–Radiation, Chromatographia (1984) 18: 265–274, No. 5.

Stober et al. Controlled Growth of Monodisperse Silica Spheres in the Micron Size Range, (1968) J. of Coll. and Interface Science 26: 62–69.

Wheals, Chemically Bonded Phases for Liquid Chromatography, J. of Chromatography (1975) 107: 402–407.

Apffel et al, 17th Intl. Symposium on the Separation of Proteins, Peptides & Polynucleotides, (Oct. 26–29, 1997).

Karin Cabrera et al., Silica ROD—A New Challenge in Fast High–Performance Liquid Chromatography Separations, Trends in Analytical Chemistry, vol. 17, No. 1, 1998, pp. 50–53.

Heftmann, Chromatography, 5th Edition Journal of Chromatography Library—vol. 51A pp. A299–A300, (1992).

Herold et al, BioChromatography, 10:5 656–662, 1991.

Huber et al., High–Resolution Liquid Chromatography od DNA Fragments on Non–Porous Poly(Styrene–Divinylbenzene) Particles, Nucleic Acids Research, vol. 21, No. 5 1061–1066.

Jinno et al., Planarity Recognition of Large Polycyclic Aromatic Hydrocarbons by Various Octadecylsilica Stationary Phases in Non–Aqueous Reverse–Phase Liquid Chrmatography Apr. 1989 pp. 285–291.

Nakanishi et al. Phase Separtion in Silica Sol–Gel System Containing Poly(ethylene oxide) I. Phase Relation and Gel Morphology, Bull Chem. Soc. Jpn., 67 1327–1335 (1994).

Nakanishi et al., Double Pore Silica Gel Monolith Applied to Liquid Chromatography, J. Sol–Gel Scince and Technology, vol. 8, 547–552 (1997).

Petro et al., Molded Monolithic Rod of Macroporous Poly(styrene–co–divinylbenzene) as a Separation Medium of HPLC . . . Anal. Chem. 1996, 68 315–321.

J. W. Goodwin et al., Colloid & Polymer Sci., 252:464–471 (1974).

J. Hirabayashi et al., Anal. Biochem., 178:336–341 (1989).

J. Hirabayashi et al., Biochemistry, 29:9515–9521 (1990).

Huber et al., Chromatographia, 37:653–658 (1993).

Y. Kato et al., J. Chromatogr., 478:264–268 (1989).

Y. Ohimya et al., Anal. Biochem., 189:126–130 (1990).

R. K. Saiki et al., Science, 230:1350–1354 (1985).

J. Ugelstad et al., Adv. Colloid Interface Sci., 13:101–140 (1980).

All–Chrom Newsletter, 25:1–6 (Jun. 1986).

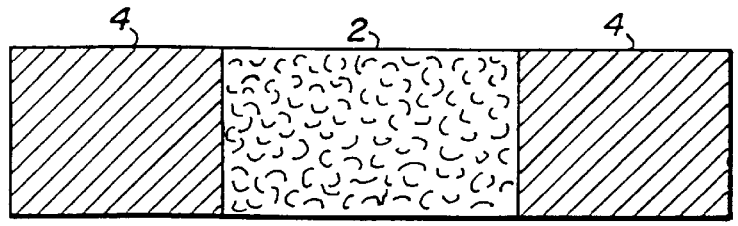
Fig_1
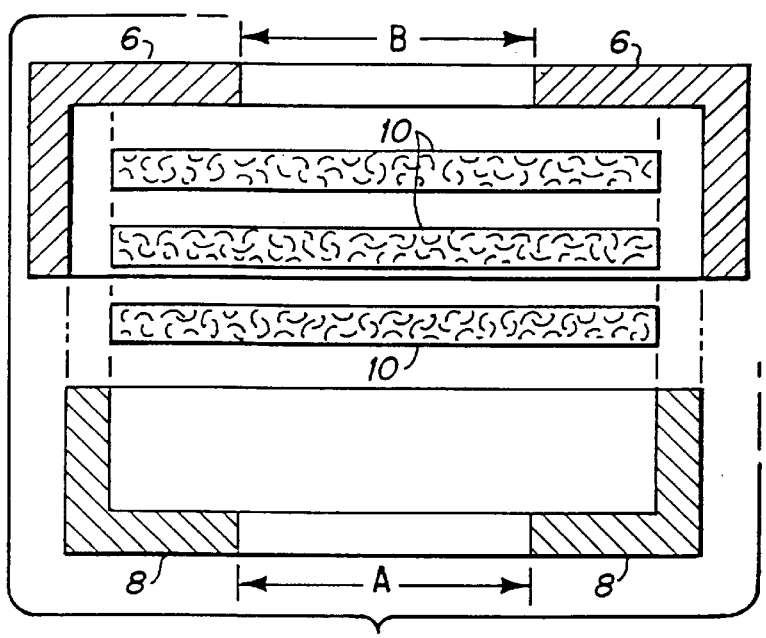
Fig_2
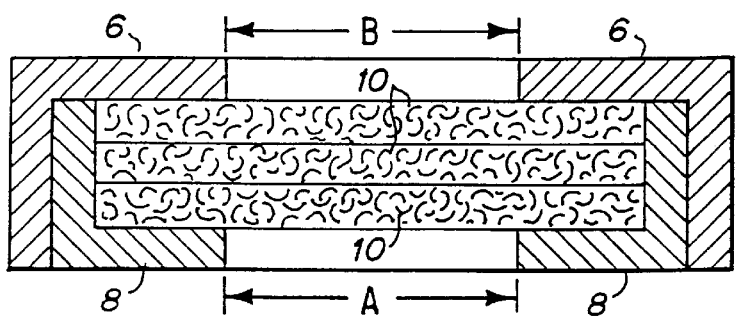
Fig_3
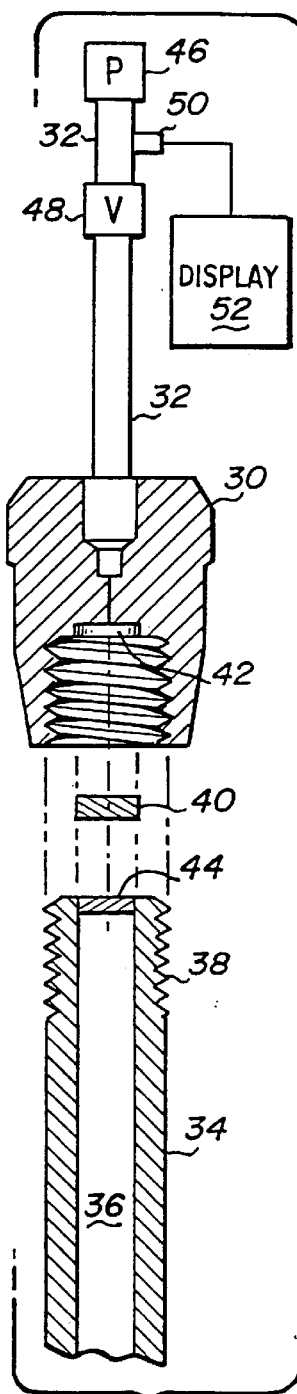
Fig_5

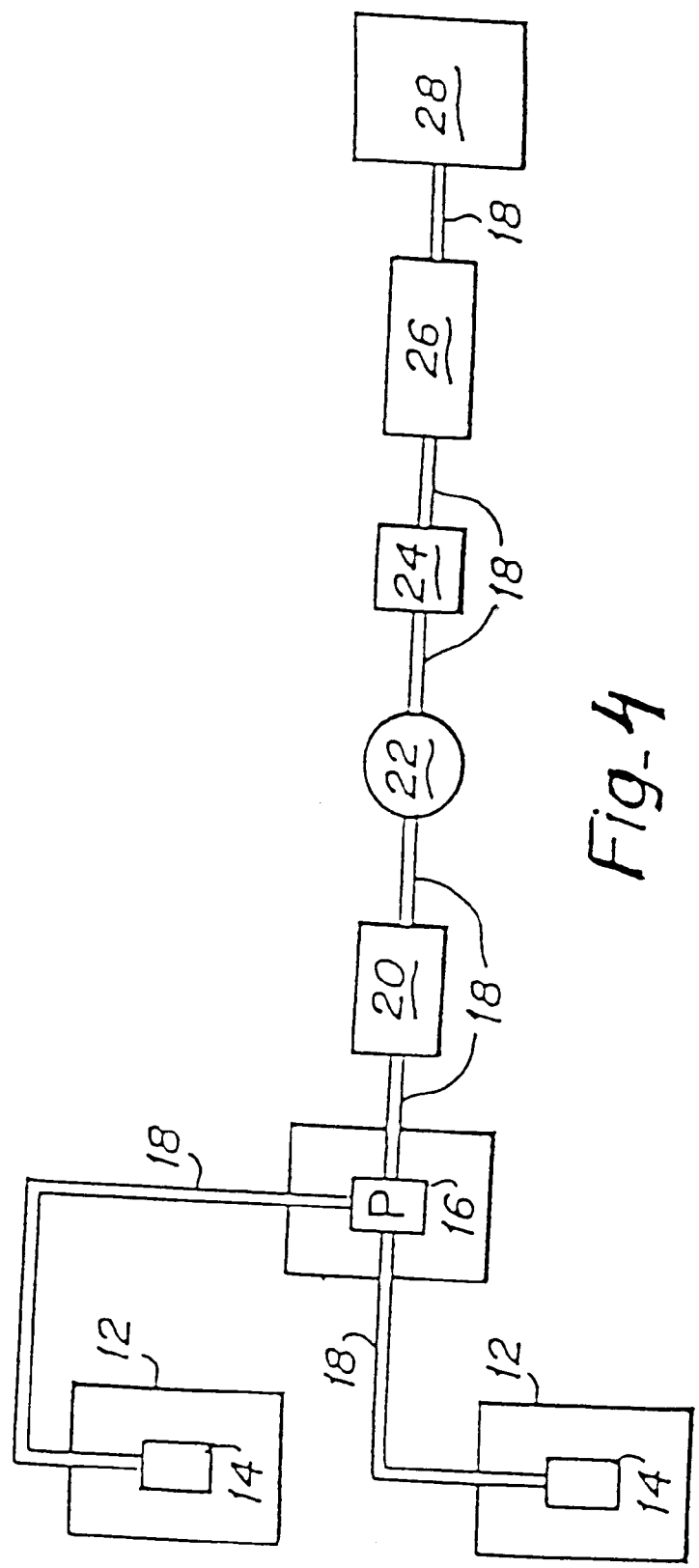

PROCESS FOR PERFORMING POLYNUCLEOTIDE SEPARATIONS

RELATIONSHIP TO COPENDING APPLICATIONS

This is a division of Ser. No. 09/081,039, filed May 18, 1998, now U.S. Pat. No. 5,972,222, which, in turn, is a continuation-in-part application of Ser. No. 08/748,376 filed Nov. 13, 1996, now U.S. Pat. No. 5,772,889. This application is filed under 35 - U.S.C. §111(a) and claims priority from commonly assigned provisional applications Ser. No. 60/049,123 filed Jun. 10, 1997; and Ser. No. 60/063,835 filed Oct. 30, 1997 under 35 U.S.C. §111(b).

FIELD OF THE INVENTION

This invention is directed to the separation of polynucleotide fragments by liquid chromatography. More specifically, the invention is directed to a system and method, which enhances the chromatographic separation of polynucleotides on non-polar, wide pore separation media.

BACKGROUND OF THE INVENTION

Separation of polynucleotide mixtures is a focus of scientific interest, and numerous researchers have been attempting to achieve technical improvements in various aspects of polynucleotide separation. Anion exchange separation and reverse phase ion pair chromatography are among the most frequently used methods for separating polynucleotide mixtures.

Samples containing mixtures of polynucleotides can result from total synthesis of polynucleotides, cleavage of DNA with restriction endonucleases or RNA, as well as polynucleotide samples which have been multiplied or amplified using polymerase chain reaction (PCR) techniques or other amplifying techniques.

Previous work has focused on developing rapid, high resolution separations, developing separations based on the size of the polynucleotide fragment rather than the base sequence of the fragment, and on developing the ability to collect separated pure fractions of polynucleotides.

W. Bloch (European patent publication No. EP 0 507 591 A2) demonstrated that, to a certain extent, length-relevant separation of polynucleotide fragments was possible on nonporous anion exchanger separation media using eluting solvents containing tetramethylammonium chloride (TMAC). Y. Ohimya et al. (*Anal Biochem.*, 189:126–130 (1990)) disclosed a method for separating polynucleotide fragments on anion exchange material carrying trimethylammonium groups. Anion exchangers with diethylaminoethyl groups were used by Y. Kato et al. to separate polynucleotide fragments (*J. Chromatogr.*, 478:264 (1989)).

U.S. Pat. No. 5,585,236 (1996) to Bonn et al. describes a method for separating polynucleotides using what was characterized as reverse phase ion pair chromatography (RPIPC) utilizing columns filled with non-polar, nonporous polymeric beads. High resolution, rapid separations were achieved using an ion pairing agent (triethylammonium acetate), and acetonitrile/water eluting solvent gradient. This work is important because it is the first example of a size dependent, sequence independent chromatographic separation of double-stranded polynucleotides by Matched Ion Polynucleotide Chromatography (MIPC). Such separations are comparable to those effected by gel electrophoresis, which is currently the technology most widely used for polynucleotide separations. Bonn's work makes it possible to automate separations of polynucleotides based on their size alone. This method differs from traditional reverse phase processes. Therefore, the term Matched Ion Polynucleotide Chromatography (MIPC) has been applied to the Bonn process to distinguish it from previously known reverse phase processes.

The invention of parent application Ser. No. 08/748,376 is based on the discovery that trace levels of multivalent metal ions, even when present below the limits of detection, interfere with the MIPC separation process. Special steps to prevent, remove or complex any trace multivalent ions result in enhanced separation of polynucleotides and lower the detection threshold. The inventions of provisional applications Ser. No. 60/049,123 filed Jun. 10, 1997; and Ser. No. 60/063,835 filed Oct. 30, 1997 under 35 U.S.C. §111(b) are based on the discovery that nitric acid passivated stainless steel, titanium, and PEEK (polyetherether ketone) surfaces were, contrary to popular belief, sources of multivalent metal ion contamination in the MIPC process. The deleterious effect of multivalent metal cations on polynucleotide separations as observed herein has not been previously reported. We believe that all chromatographic processes which are capable of separating polynucleotides on non-polar, wide pore separation media are impaired by the interference of multivalent metal ions.

SUMMARY OF THE INVENTION

Therefore, the invention provides an improved method for separating a mixture of polynucleotide fragments wherein multivalent cations are eliminated from the all aspects of the separation process. The method comprises applying a solution of said fragments and counterion agent to a column containing separation media having a non-polar surface, wherein said separation media have a pore size greater than 30 Angstroms and an average diameter of 1–100 microns. Separation of said fragments is accomplished by eluting said fragments with an eluting solvent gradient of increasing organic component concentration containing a counterion agent. Surfaces which are contacted by the solution of the fragments and the eluting solvent are materials which do not release multivalent metal cations therefrom, said materials having been washed to remove traces of organic contaminants therefrom. The method further comprises contacting the solution of said fragments and the eluting solvent with a multivalent cation capture resin to remove any multivalent cations therein before entering the column.

In a preferred embodiment of the invention, the separation media have been treated to remove residual traces of multivalent cations from the surfaces therefrom.

An optimum embodiment of the invention comprises contacting the solution of said fragments and eluting solvent with a multivalent cation capture resin before entering the column, treating the separation media to remove residual traces of multivalent cations from the surfaces therefrom, and ensuring that surfaces which are contacted by the solution of the fragments and the eluting solvent are materials which do not release multivalent metal cations therefrom and cleaning said surfaces to remove any traces of organic contaminants therefrom.

In one embodiment, the polynucleotide fragments are double stranded, having more than 5 base pairs. Such fragments are separated by size or by polarity.

In another embodiment of the invention, the polynucleotide fragments are single stranded having 2 or more nucleotides. Such fragments are separated by size and by polarity.

The separation media are organic polymer, or an inorganic substrate selected from the group consisting of inorganic substrates, silica, zirconia, and alumina. The inorganic substrates support a non-polar material on their surface. Said non-polar material may be organic polymer or long chain, C1 to C24 hydrocarbon groups bound to the inorganic substrate, wherein residual polar groups of the substrate are end capped with trimethylsilyl chloride or hexamethyldisilazane.

In a preferred embodiment, surfaces which are contacted by the solution of polynucleotide fragments and eluting solvent are titanium, coated stainless steel, organic polymer or combinations thereof. Removal of traces of residual multivalent metal cations from the separation process is further ensured by treating said surfaces with a solution comprising aqueous acid and chelating agent, by adding a chelating agent to the solution of polynucleotide mixture and eluting solvent, and by treating the eluting solvent to remove oxygen therefrom.

In one embodiment, the improved method for separating said mixture of polynucleotides comprises Matched Ion Polynucleotide Chromatography.

The improved method of the invention may also be practiced as a batch process for separating polynucleotide fragments having a selected size from a mixture of polynucleotide fragments including fragments of said selected size. The batch process method of the invention comprises applying a solution of said polynucleotide fragments and a counterion agent to non-polar separation media having a non-polar surface, wherein said separation media have a pore size greater than 30 Angstroms and an average diameter of 1–100 microns. The method further comprises contacting the separation media with a first eluting solvent and counterion agent, the first eluting solvent having a concentration of organic component sufficient to release from the separation media all polynucleotide fragments having a size smaller than the selected size and removing the first eluting solvent from the separation media. The selected size fragments are obtained by contacting the separation media with a second eluting solvent having a concentration of organic component sufficient to release from the separation media the polynucleotide fragments having the selected size and removing the second eluting solvent from the separation media. Preferably, surfaces which are contacted by the solution of polynucleotide fragments and the eluting solvent are material which does not release multivalent metal cations therefrom.

Following removal of the first eluting solvent, the separation media are rinsed with fresh first eluting solvent to remove residual released polynucleotide fragments therefrom. In a similar manner, following removal of the second eluting solvent the separation media are rinsed with fresh second eluting solvent to remove residual released polynucleotide fragments of selected size therefrom.

A preferred embodiment of the invention comprises contacting the solution of polynucleotide mixture and eluting solvent with a multivalent cation capture resin before contacting the separation media. In another preferred embodiment the method comprises treating the separation media to remove residual traces of multivalent cations therefrom. Optimally the separation media have been treated to remove residual traces of multivalent cations therefrom and the solution of polynucleotide mixture and eluting solvent have been contacted with a multivalent cation capture resin before contacting the separation media. Said separation media are contained in a column, a web, a membrane, or container.

The batch process can be used to separate mixtures of double stranded polynucleotides or single stranded polynucleotides.

The separation media are organic polymer, or an inorganic substrate selected from the group consisting of inorganic substrates, silica, zirconia, and alumina. The inorganic substrates support a non-polar material on their surface. Said non-polar material may be organic polymer or long chain, C1 to C24 hydrocarbon groups bound to the inorganic substrate, wherein residual polar groups of the substrate are end capped with trimethylsilyl chloride or hexamethyldisilazane.

The surfaces contacted by the solution of polynucleotide fragments and eluting solvent are, preferably, comprised of material selected from the group consisting of titanium, coated stainless steel, and organic polymer, or combinations thereof. Removal of traces of residual multivalent metal cations from the separation process is further ensured by treating said surfaces with a solution comprising aqueous acid and chelating agent, by adding a chelating agent to the solution of polynucleotide mixture and eluting solvent, and by treating the eluting solvent to remove oxygen therefrom.

BRIEF DESCRIPTION OF THE DRAWINGS

FIG. 1 shows a guard disk having a one-piece annular ring.

FIG. 2 is an exploded view of a guard disk having a two-piece annular ring and containing three pads of guard disk material (i.e., a layer or pad of multivalent cation capture resin which has been incorporated into a fabric or membrane).

FIG. 3 shows an assembled view of the guard disk of FIG. 2.

FIG. 4 shows placement of a chelating guard column and chelating guard disk in a liquid chromatographic system for polynucleotide separation.

FIG. 5 shows placement of a chelating guard disk positioned between a chromatographic separation column and a column top, where the guard disk is in direct contact with a titanium frit at the top portion of the separation column.

DETAILED DESCRIPTION OF THE INVENTION

Figure 6:
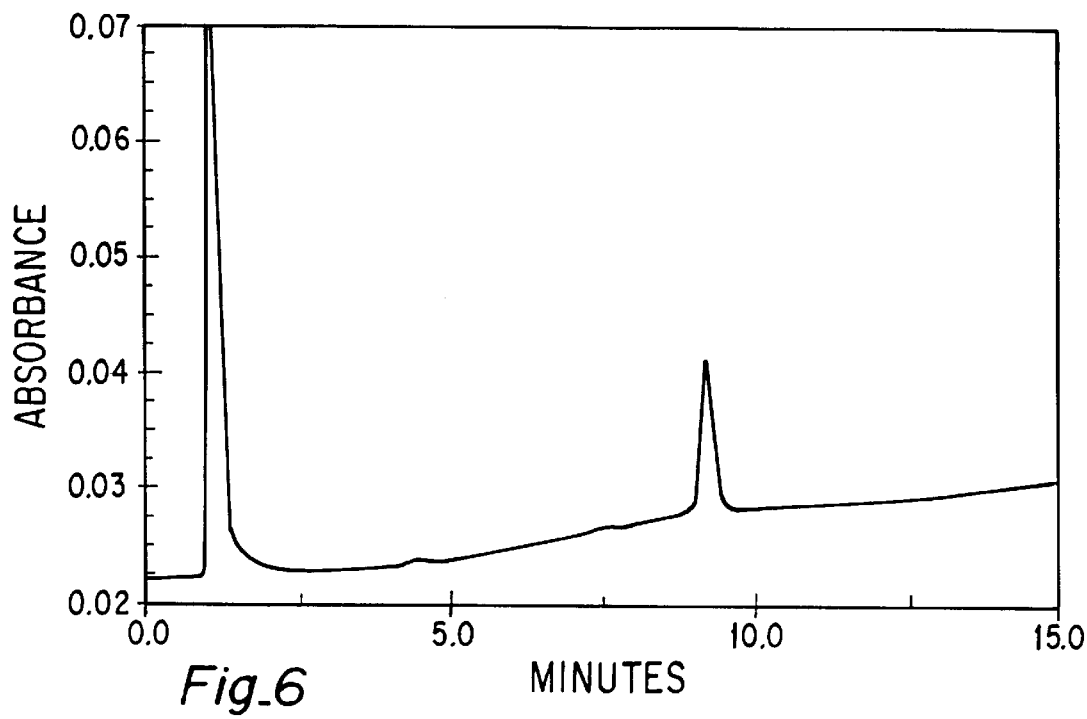
FIG. 6 shows the chromatography of a 500 base pair DNA fragment on PRX-1 (Sarasep, San Jose, Calif.) non-polar, wide pore polymer separation media which have been washed (see Example 1) to remove multivalent metal cations therefrom.

The term polynucleotide, as used herein, is defined as a linear polymer containing an indefinite number of nucleotides, linked from one ribose (or deoxyribose) to another via phosphate residues. The present invention can be used in the separation of RNA or of double or single stranded DNA. For purposes of simplifying the description of the invention and not by way of limitation, the separation of double stranded DNA will be described hereinafter, it being understood that all polynucleotides are intended to be included within the scope of this invention.

The present invention is an improved chromatographic and batch process method for separating mixtures of polynucleotide fragments on wide pore non-polar separation media. The improvement comprises ensuring the removal of all traces of residual multivalent metal cations from the sample mixture, the eluting solvent as well as components of the chromatographic or batch process equipment which contact said sample mixture and eluting solvent. The inventor's observation and demonstration that even traces of multivalent metal cations below the level of detection, degrade polynucleotide separations on wide pore, non-polar separation media and that removal of said cations results in improved separation efficiency and column life is both surprising and novel.

The system used to implement the method of the invention comprises a liquid chromatographic system. The liquid chromatography system comprises a column containing a separation bed of non-polar, wide pore separation media held in the column between porous frits positioned at each end of the column. Other components of the liquid chromatography system include an injection valve and one or more eluting solvent supply means. Eluting solvent supply means is (are) connected to the injection valve, and the injection valve is connected to the inlet of the chromatographic separation column, by means of conduit (e.g., tubing), as illustrated in FIG. 5.

The chromatography system components mentioned hereinabove and variations thereof are well known in the chromatography art and described in detail in references cited hereinbelow.

In a preferred embodiment of the invention, the mixture of polynucleotide fragments is separated by Matched Ion Polynucleotide Chromatography (MIPC). The term "Matched Ion Polynucleotide Chromatography" as used herein is defined as a process for separating single and double stranded polynucleotides using non-polar, wide pore separation media, wherein the process uses a counterion agent, and an organic solvent to release the polynucleotides from the separation media.

The pores of the separation media may be contiguous, i.e., extend from one surface of the media to another surface of the media. The pores of the separation media may also be non-contiguous, i.e., extend into the media at one point on the surface but not through to another point on the surface.

The non-polar, wide pore separation media can be an inorganic substrate, including silica, zirconia, alumina, or other material; or can be polymeric, including crosslinked resins of polystyrene, polyacrylates, polyethylene, or other organic polymeric material. The non-polar, wide pore separation media can also be a "rod column" or "monolith column". Such columns contain silica or polymer separation media which have been formed inside the column as a continuous structure which has through pores or interstitial spaces which allow eluting solvent and analyte to pass through. The only requirement for the non-polar, wide pore separation media is that they must have a surface that is either intrinsically hydrophobic or be bonded with a material that forms a surface having sufficient hydrophobicity to interact with a counterion agent.

As used herein, the term "non-polar, wide pore separation medium" is defined to denote any material which has surface pores having a diameter that is greater than 30 Angstroms or the approximate size and shape of the smallest polynucleotide fragment in the separation in the solvent medium used therein or greater, and is capable of separating polynucleotide fragments. Although the non-polar, wide pore separation medium may be any shape, those comprising alkylated wide pore polymer beads bead having an average diameter of 1–100 microns are preferred. Such particles are described in the references cited hereinbelow.

Regardless of the source or composition of the non-polar, wide pore reverse phase separation media described above, special precautions are taken to ensure that they are substantially free of multivalent cation contaminants. For example, the separation media are washed with acid followed by methanol to ensure removal of residual multivalent cation contaminants. The separation media can also be washed with EDTA or other chelating agent.

The concepts, materials, systems and methods related to chromatography on non-polar, wide pore separation media are well known and are described in detail in the following references: Chromatography Today, by Colin F. Poole and Salwa K. Pool, Elsevier (1991); Introduction to Modern Liquid Chromatography, L. R. Snyder and J. J. Kirland, J. Wiley and Sons, Inc. (1979). These references and references contained therein are incorporated in their entirety herein.

Non-polar, wide pore separation media and their use for the separation of polynucleotide mixtures are well known in the art and are commercially available, e.g., Hamilton HPLC Application Handbook, (1993), Hamilton Company, Inc., 4970 Energy Way, Reno, Nev. 89502. This, and references contained therein, are incorporated in their entirety herein. Another reference, which is incorporated in its entirety herein, describing polynucleotide separations on non-polar, wide pore separation media is Chromatography, 5th edition, Part B, edited by E. Heftmann, Elsevier (1992). Separation of tRNA and DNA fragment mixtures on non-polar, wide pore silica particles is described by R. Bischoff and L. W. McLaughlin, Analytical Biochemistry, 155, 526–533 (1985) and S. Eriksson, et. al., J. Chromatography, 359, 265–274 (1986).

Monolith or rod columns are commercially avialable form Merck & Co (Darmstadt, Germany) and described in the following references: U.S. Pat. No. 5453185 to J. M. J. Frechet and F. Svec; M. Petro, et. al., Analytical Chemistry, 68, 315–321 (1996). The references cited above and the references contained therein are incorporated in their entirety herein.

The components of the liquid chromatography system have surfaces (i.e., "process solution contacting surfaces")

which contact process solutions held within the components (e.g., the eluting solvent supply means) or flowing through the components (e.g., the porous frits, chromatographic column, injection valve, and conduits). The term "process solution" as used herein refers to any solution (such as the polynucleotide mixture solution and the eluting solvent) which is contained within or flows through any component of the liquid chromatography system during the chromatographic process. The term "process solution contacting surface" refers to any surface of a liquid chromatography system which contacts said process solutions.

The process solution contacting surfaces of the porous frits on either end of the separation column must be made of material which does not release multivalent cations into solutions flowing through the column, or collect said cations from other sources. The material is preferably titanium, coated stainless steel, or organic polymer, or combinations thereof, but is most preferably acid treated titanium as described hereinbelow. The term "coated stainless steel" as used herein refers to stainless steel that has been coated so that it does not release, or is prevented from releasing, multivalent cations. A non-limiting example of a coating material is polytetrafluoroethylene (i.e., Teflon®). "Coated stainless steel" as used herein also refers to stainless steel that has been pre-treated with an agent such as EDTA or phosphoric acid which forms coordination complexes with multivalent metal ions.

"Passivated stainless steel" as used herein refers to stainless steel that has been treated with an agent that removes oxidized metals and also metals that are easily oxidized such as iron. The most common passivating agent for stainless steel is nitric acid. Nitric acid will removed any oxidized metals, but will also remove iron that is located on the surface of the metal, leaving other metals such as chromium and nickel. Some chelating agents can coat and passivate. EDTA will first coat oxidized metals especially colloidal iron oxide particles. As treatment continues, the EDTA will bind and dissolve the iron oxide. However, as individual iron molecules leave the particle, other chelating molecules must coat the newly exposed surfaces for the surface to remain suitable for polynucleotide separations. A chelating agent does not passivate in the sense that it will only coat metal ions for which it is specific and will not dissolve non-oxidized metals. However, a chelating agent may, eventually, dissolve oxidized metals.

The chelating agents used depend upon the type of ion contamination which is present. For example, Tiron chelating agent is selective for titanium and iron oxides. EDTA is selective for most metal oxides at pH 7. Other chelating agents include cupferron, 8 hydroxyquinoline, oxine, and various iminodiacetic acid derivatives. If the chelating agents are to be used as passivating reagents as well as coating reagents, then it is important that the metal ion chelate complex, for example, EDTA-metal ion complex, is soluble in the fluid. Chelating agents that form insoluble complexes, for example 8-hydroxyquinoline, perform coating functions only.

Without wishing to be bound by theory, it is believed that oxidized and positively charged metals, such as oxides of iron on the surface of stainless steel can trap negatively charged molecules such as DNA leading to degradation of the chromatographic separation, and that the pre-treatment masks or shields these surface charges. EDTA can be added, for example, in an amount sufficient to shield any surface sites which would interfere with the chromatographic separation. In one embodiment, a solution of a metal chelating agent such as EDTA can be applied in a batch process to coat the surface, for example by a single injection of EDTA solution into the HPLC system. In another embodiment, EDTA is included as an additive in the eluting solvent in an amount sufficient to complex the metal ions present.

Other components of the liquid chromatography system are preferably titanium, coated stainless steel, or organic polymer such as polyetherether ketone (PEEK) or polyethylene. The preferred system tubing (i.e., conduit) is titanium, PEEK, or other polymeric material, with an inner diameter of 0.007". The preferred eluting solvent inlet filters are composed of non-polar, porous, non-stainless steel material, which can be PEEK, polyethylene, or other polymeric material. The preferred solvent pump is also made of a non-stainless steel material; the pump heads, check valves, and solvent filters are preferably titanium, PEEK, or other polymeric material. The preferred means for removing oxygen from the eluting solvent is an inline degasser placed prior to the pump inlet. The sample injection valve is also preferably titanium, PEEK, or other polymeric material. A standard detector and eluting solvent reservoirs can be used, with no modifications necessary.

Materials such as titanium, PEEK and other organic polymers such as polyethylene, have been generally considered to be inert and preferred for the chromatographic separation of biological molecules. We have discovered that these materials, while inert for the prior art processes, can be a source of contaminants which interfere with the chromatographic separation of polynucleotides on non-polar, wide pore separation media. We have also observed that the interference with separation of polynucleotides by these materials becomes more apparent during separations carried out at elevated temperatures, e.g. 56° C. as compared to 50° C.

In a preferred embodiment of the present invention, all of the process solution-contacting surfaces are subjected to a multivalent cation removal treatment to remove any potential source of multivalent cation contamination. These surfaces include the column inner surface, porous frits, conduits, eluting solvent supply system, injector valves, mixers, pump heads, and fittings. A non-limiting example of a multivalent cation removal treatment is an acid wash treatment. This wash treatment can include flushing or soaking and can include sonication. An example of an acid wash treatment is sonication of a PEEK or titanium frit in the presence of aqueous nitric acid solution, followed by sonication in water until a neutral pH is achieved. Other treatments include contacting the surfaces with chelating agents such as EDTA, pyrophosphoric acid, or phosphoric acid (e.g. 30% by weight phosphoric acid).

PEEK and titanium can be treated with dilute acids including nitric and hydrochloric acids. PEEK is not compatible with concentrated sulfuric or concentrated nitric acids. Titanium is not compatible with concentrated hot hydrochloric acid. Treatment with a chelating agent can be performed before, but preferably after treatment with an acid. 20 mM tetrasodium EDTA is a preferred chelating agent treatment.

The preferred treatment for titanium frits is sonication for 10 minutes with cold hydrochloric acid, sonication with water until neutral pH, 2 hour sonication with 0.5 M tetrasodium EDTA, storage several days in 0.5 M tetrasodium EDTA, sonication with water until neutral pH, and then washing with methanol, followed by drying. Preferred treatment for PEEK frits is sonication for 15–30 minutes each with THF, concentrated hydrochloric acid, 20% nitric acid, sonication with water until neutral pH, and then washing with methanol, followed by drying. Although this is a preferred treatment method, the effectiveness of this treatment of PEEK frits can depend on the vendor and lot of material treated. The success of the treatment also depends on the temperature of the polynucleotide separation with higher column temperatures requiring the most complete removal of contamination. If the ionic contaminant is organic, then organic solvents or a combination of organic solvents and acids can be used. Also, organic ionic contaminants can require detergents, soaps or surfactants for removal from the surface.

Nonionic contaminants such as greases and oils will also contaminate the separation column, generally leading to poor peak shape, but depending upon the size of the fragment. Nonionic organic contaminants such as oils will require detergents, soaps or surfactants to remove. Column tubing can be treated under sonication with Decalin (D5039, Sigma) to remove silicon greases and oils. Removal of colloidal metal oxides such as colloidal iron oxide can require repeated or continuous treatment as the surface of the particle is dissolved and new metal oxides are exposed.

The preferred embodiment of the liquid chromatography system of the present invention utilizes methods to minimize the exposure of all process solution contacting surfaces to oxygen. Dissolved oxygen within the eluting solvent, for example, can react with exposed metals on these surfaces to form oxides which will interfere with the chromatographic separation.

The liquid chromatography system preferably employs a degassing method for essentially removing dissolved oxygen from the eluting solvent prior to contact with the rest of the chromatography system. Examples of degassing methods include sparging of the eluting solvent with an inert gas such as argon or helium, or filtering the eluting solvent under vacuum. A preferred method uses a vacuum type degasser which employs inline passage of the eluting solvent over one side of an oxygen permeable membrane system where the other side is subjected to a vacuum. An example of a suitable four channel vacuum type degasser is Degaset™, Model 6324 (MetaChem Technologies, Torrance, Calif.).

In another embodiment of the invention, a stainless steel HPLC system can be used if a component for removing multivalent cations, herein referred to as a "multivalent cation capture resin," is also used. A multivalent cation capture resin is preferably a cation exchange resin or chelating resin. Any suitable cation exchange resin or chelating resin can be used. Preferred cation exchange and chelating resins are described hereinbelow.

Cation exchange resins having an ion exchange moiety selected from the group consisting of iminodiacetate, nitriloacetate, acetylacetone, arsenazo, hydroxypyridinone, and 8-hydroxyquinoline groups are particularly preferred. Cation exchange resins having hydroxypyridinone groups are especially useful for removing iron from the system. Cation exchange resins having iminodiacetate groups are particularly preferred for use in the present invention because of their wide availability in resin format.

A chelating (i.e., coordination binding) resin is an organic compound which is capable of forming more than one non-covalent bond with a metal. Chelating resins include iminodiacetate and crown ethers. Crown ethers are cyclic oligomers of ethylene oxide which are able to interact strongly with alkali or alkaline earth cations and certain transition metal cations. A cavity in the center of the molecule is lined with oxygen atoms which hold cations by electrostatic attraction. Each ether has a strong preference for cations whose ionic radius best fits the cavity.

The multivalent cation capture resin is preferably contained in a guard column, guard cartridge, or guard disk. Guard columns and cartridges are frequently used to protect liquid chromatography columns from contamination and are widely available. In their normal use, guard columns and cartridges typically contain packing material which is similar to the stationary phase of the separation column. However, for use in the present invention, the guard column or cartridge must contain a multivalent cation capture resin. The guard disc or guard column must contain particles which trap the metal ions.

For use in the system of the present invention, the guard cartridge or column should be sufficiently large to provide adequate cation capture capacity, but must be small enough to allow effective gradient elution to be used. A preferred guard cartridge has a void volume of less than 5 mL, more preferably, less than 1 mL, so that the eluting solvent gradient is not delayed by more than 5 minutes and, preferably, less than 1 minute. The preferred cartridge has a 10×3.2 mm bed volume.

Guard disks are described in detail in U.S. Pat. No. 5,338,448, which is incorporated herein by reference in its entirety. For use in the present invention, a guard disk comprises a layer or pad of a multivalent cation capture resin which has been incorporated into a fabric or membrane so that the resin is not separable from the guard disk under liquid flow conditions present during the performance of chromatographic separations.

In its preferred form, the guard disk is circular, having a rigid annular outer ring or collar for easy handling. The annular ring can be constructed of any suitable material which is inert to the chromatographic separation, such as inert conventional engineering plastic. The only requirement for the material is that it must be inert to the eluting solvent and sample and have sufficient dimensional stability. The rigid annular outer ring of the guard disk can comprise a single rigid annular outer ring encircling a disk-shaped pad of guard disk material. As used herein, the term "guard disk material" refers to a layer or pad of multivalent cation capture resin which has been incorporated into a fabric or membrane.

As shown in FIG. 1, one or more pads of guard disk material 2 are placed in the rigid annular ring 4. For example, the fabric can be cut to a circular diameter which securely contacts the inner diameter surface of the annular ring. As the disk holder is tightened against the disk, the top and bottom surfaces of the holder seal against the collar of the guard disk. Sealing pressure from the guard disk holder is, therefore, applied against the collar of the disk which prevents the material of the guard disk pad from being crushed.

Alternatively, the rigid annular outer ring can comprise two flanged rings, as shown in FIG. 2 and 3, an outer flanged ring 6 and an inner flanged ring 8, where the inner flanged ring is insertable within the flange of the outer ring, forming a press-fit two-piece collar around one or more pads of guard disk material 10. Preferably, the inner diameter (a) of the inner flanged ring will have the same diameter as the separation column bed.

In the two-piece annular ring embodiment shown in FIG. 3, one or more pads of guard disk material 10 having a diameter greater than the inner diameter (b) of the outer flanged ring 6 are positioned within the flanges of the outer ring. The inner flanged ring 8 is then inserted into the outer ring to form a press-fit two-piece annular ring in which the guard disk pad(s) is (are) frictionally held within the press-fit ring or collar. Preferably, the inner diameter (b) of the outer flanged ring and the inner diameter (a) of the inner flanged ring are substantially the same.

Alternatively, the rigid annular outer ring can be incorporated into the guard disk holder or chromatographic column cap. The annular ring is a flange that is part of one or both sides of the disk holder or the column cap. In this case, the guard disk does not have an outer ring. A circle of the guard disk sheet material is placed into the holder or column cap. The flange in the holder column cap is annular so that, when the holder or column cap is tightened, the flange pinches or seals the outer annular portion of the guard disk. The center portion of the guard disk not pinched is in a chamber or depression in the holder or cap. Fluid flows through the center portion, allowing the guard disk to retain particulate or strongly adsorbed material, but fluid cannot flow around the disk or past the edges. The function of the guard disk is exactly the same as when the collar is part of the guard disk itself. However, in this case, the collar is part of the holder or column cap.

In a most preferred embodiment of the invention, a multivalent cation capture resin contained in a guard column, guard cartridge, or guard disk is placed upstream of the separation column. Most preferably, the guard column, cartridge, or disk containing the resin is placed upstream of the sample injection valve. Although this is preferably a guard disk, a guard cartridge or column can be used as long as the dead volume of the cartridge or column is not excessive and an effective eluting solvent gradient can be produced.

Optimally, a guard disk, column, or cartridge can be placed before the injection valve and a second guard disk, column, or cartridge also placed between the sample injection valve and the separation column. In certain cases, the second guard disk (or cartridge or column) can be avoided if the contaminants are sufficiently cleaned by a guard column placed upstream of the injection valve, or if the contaminants are avoided through the use of non-metal or titanium components throughout the HPLC system.

Placement of a chelating guard column and chelating guard disk in a liquid chromatography system for polynucleotide separation is illustrated in FIG. 4. The eluting solvent reservoirs 12 contain eluting solvent inlet filters 14 which are connected to the solvent pump 16 by system tubing 18. The solvent pump 16 is connected to a chelating column 20 by system tubing 18. The chelating column 20 is connected to the sample injection valve 22 by system tubing 18. The sample injection valve has means for injecting a sample (not shown). The sample injection valve 22 is connected to a chelating guard disk 24 by system tubing 18. The chelating guard disk 24 is connected to the inlet (not shown) of the separation column 26 by system tubing 18. Detector 28 is connected to the separation column 26. As discussed above, the system tubing, eluting solvent inlet filters, solvent pump, sample injection valve, and separation column are preferably made of titanium, coated stainless steel, or organic polymer. The material is preferably treated so that it does not release multivalent cations. The treatment can include treatment with nitric acid, phosphoric acid, pyrophosphoric acid, or chelating agents. In cases, where components of the HPLC do not release metal ion contaminants and are suitable for polynucleotide separations in general and MIPC in particular, then use of the chelating cation exchange guard column or guard disc is not necessary.

In operation, eluting solvent from the eluting solvent reservoirs 12 is pumped through eluting solvent inlet filters 14 by solvent pump 16. By way of system tubing 18, the eluting solvent stream flows through chelating column 20, through sample injection valve 22, through chelating guard disk 24, then into separation column 26. Detector 28 is located downstream from separation column 26.

FIG. 5 illustrates a specific embodiment of the invention in which a chelating guard disk is placed in direct contact with a titanium frit at the top portion of a chromatographic separation column. Column top 30 has conventional fittings for receiving eluting solvent and sample through inlet tubing 32. The column top or cap 30 is fitted and sealably attached to column body 34 containing chromatographic bed 36 using a conventional fitting 38 (e.g., threaded) or any equivalent fitting capable of tightly sealing the column top to the column body. The column top 30 is adapted to receive the chelating guard disk 40 in a sealing cavity 42. In this embodiment, the guard disk 40 is in direct contact with a titanium column frit 44, which is located at the upstream end of the column body 34 to prevent disturbance of the chromatographic bed 36 when the column top 30 is removed to observe the guard disk.

In operation, solvent pump 46 pumps elution solvent to sample injection valve 48 into column top 30 through chelating guard disk 40 and then through titanium frit 44 before entering chromatographic bed 36. Eluting solvent pressure upstream from the guard disk is measured by pressure transducer 50 which is electrically connected to a display device 52.

As discussed above, a chelating guard column, cartridge, or disk can be used in conjunction with a conventional, stainless steel liquid chromatography system, or with a system containing non-metal or titanium components in order to provide extra protection against ionic contaminants. For additional column protection, an eluting solvent containing 0.1 mM tetrasodium EDTA or other chelating solution can be used during the performance of polynucleotide separations.

In another aspect of the invention the non-polar, wide pore separation media have been washed to remove any traces of residual multivalent metal cations from the surface thereof. Preferred washing solvents comprise tetrahydrofuran, hydrochloric acid, and water. An example of a preferred washing procedure is described in Example 1.

The methods of the invention comprise using the improved systems described above to separate mixtures of polynucleotide fragments, particularly double-stranded polynucleotide fragments. The methods of the present invention can be used to separate polynucleotide fragments having up to about 1500 base pairs using non-polar, wide pore separation media under the chromatography conditions described herein.

The most preferred method of the invention comprises contacting a solution of a mixture of polynucleotide fragments containing a counterion agent with a multivalent metal cation capture resin, followed by application of said solution to a separation column containing non-polar, wide pore separation media wherein said particles have been washed to remove any traces of residual multivalent cation therefrom. Optimally, the process solution contact surfaces of the system have been passivated, as described hereinabove, to remove multivalent metal cations therefrom. In an optimum configuration, a guard cartridge or guard column containing multivalent cation capture resin is placed at the front of the column or in line between the eluting solvent reservoir and the solvent pump(s) to protect said column and the separation media contained therein from any traces of residual multivalent metal cations in the eluting solvent. The polynucleotide fragments are separated by releasing said fragments from the separation media using an eluting solvent comprising an organic component, water, and a counterion agent. The separation of the polynucleotide components is based on the size or polarity of the fragments. By way of example only, the fragments are released from the separation media in order of size by increasing the concentration of organic component in the eluting solvent. The concentration of the organic component can be increased in stepwise fashion by means of a step gradient, or continuously, by means of a continuous gradient.

The methods used to capture multivalent cations and prevent their presence in the chromatography system, are essential in order to achieve high resolution separations of polynucleotides, especially double stranded DNA, and also to greatly extend the useful life of the separation media. Evidence demonstrating the detrimental effect of multivalent metal cation contamination on the chromatographic separation of both single stranded polynucleotide fragments and double stranded polynucleotide fragments on non-polar, wide pore silica and polymer separation media is presented in Examples 2–7 and FIGS. 6–15.

Example 2 describes a polynucleotide fragment separation on non-polar, wide pore organic polymer separation media using the optimized method of the invention compared to a deliberate contamination of the system with multivalent metal cations. While a sharp peak is obtained using the optimized method of the invention, the peak is completely absent when the chromatography system was deliberately contaminated with multivalent metal cations.

Example 3 is identical to Example 2, except that non-polar, wide pore silica separation media were used in the chromatography.

Figure 7:
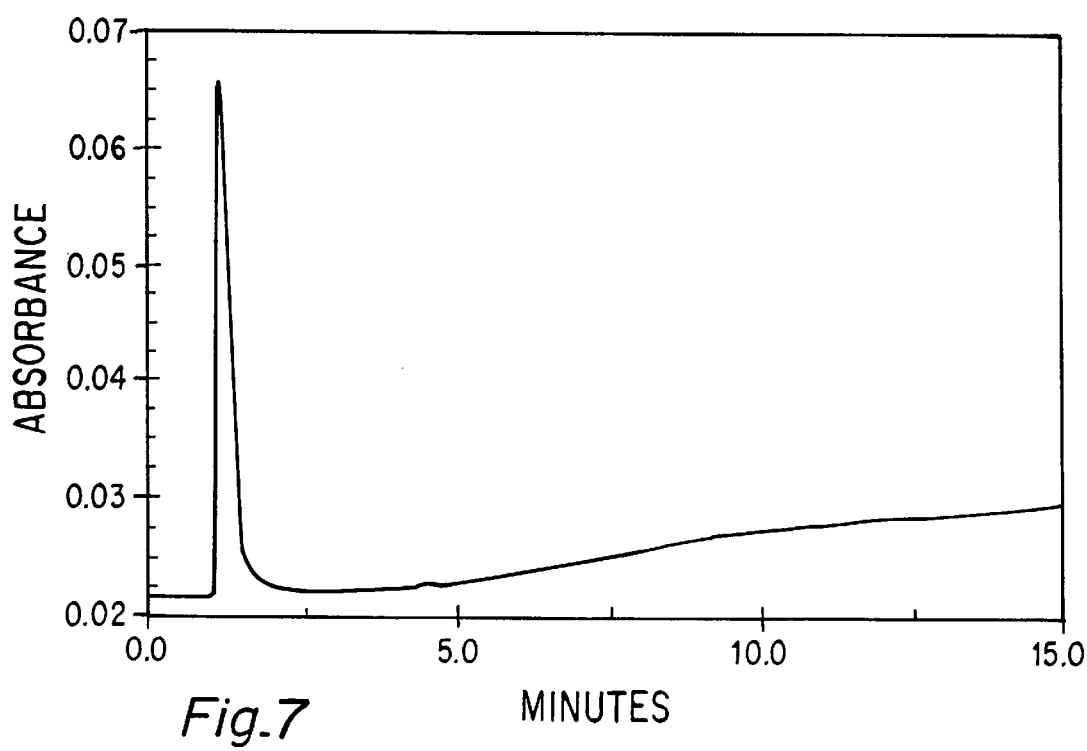
FIG. 7 shows the effect on the chromatography result shown in FIG. 6 hen Cr(III) cations were added to the column before sample injection.
Figure 8:
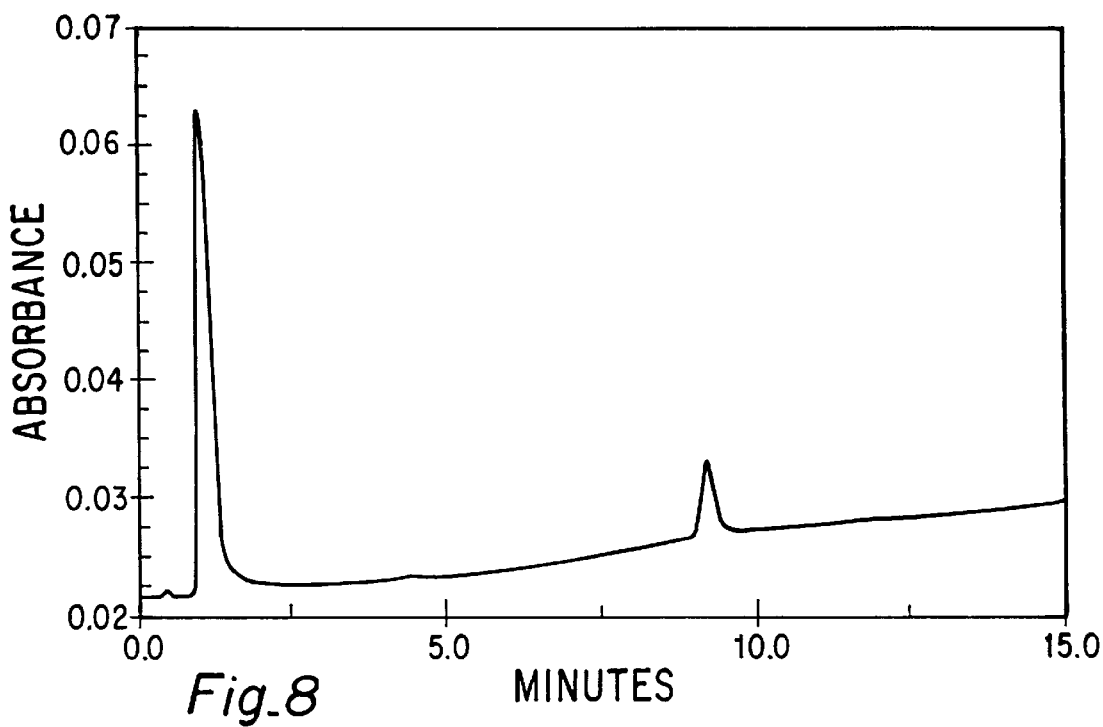
FIG. 8 shows the effect on the chromatography result of FIG. 7 when a Cr(III) contaminated column was treated with EDTA prior to sample injection.

In Example 4, a series of three separations of a 500 base pair DNA fragment was performed using non-polar, wide pore polymer separation media are described. In the first separation, the separation media was washed to remove multivalent cations as described in Example 1 prior to sample injection, and a sharp peak was obtained as shown in FIG. 6. Deliberate contamination of this separation media with Cr (III) cations resulted in a complete loss of the sample peak as shown in FIG. 7. Treatment of the separation particles with EDTA solution to remove the Cr (III) and any other ions which may have been present, partially restored the sample peak as shown in FIG. 8.

Figure 9:
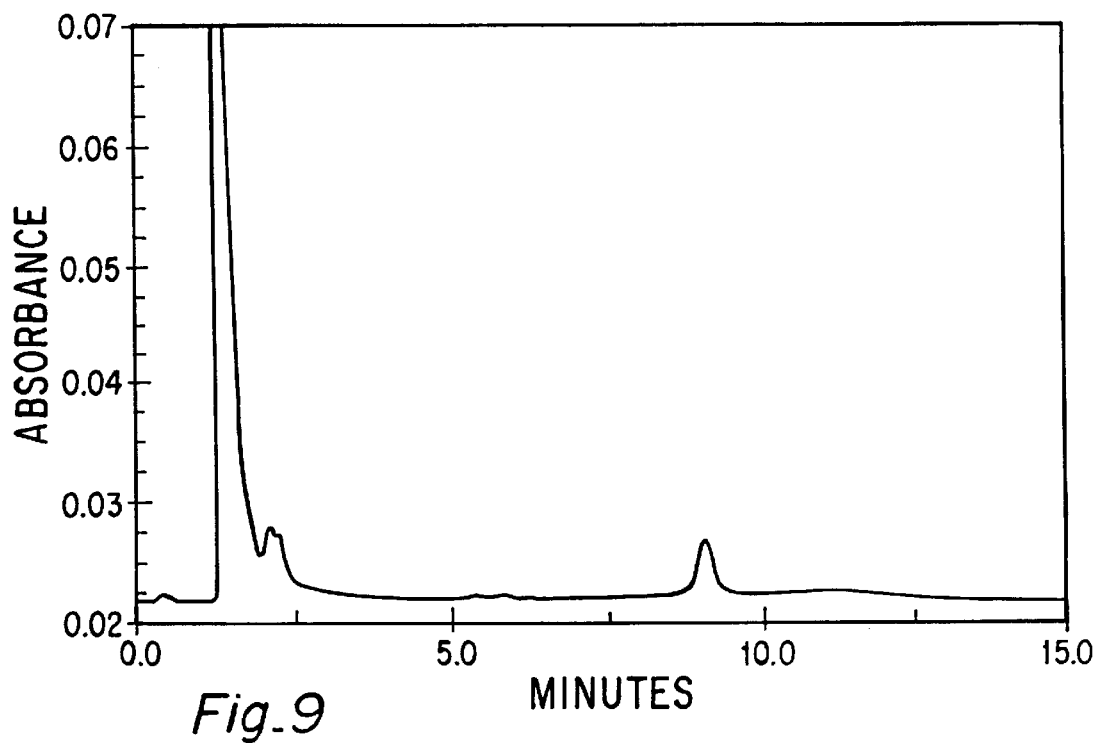
FIG. 9 shows the chromatography of a 500 base pair DNA fragment on INERTSIL (MetaChem, Torrance, Calif.) C-18 non-polar, wide pore silica separation media which have been washed with EDTA to remove multivalent metal cations therefrom.
Figure 10:
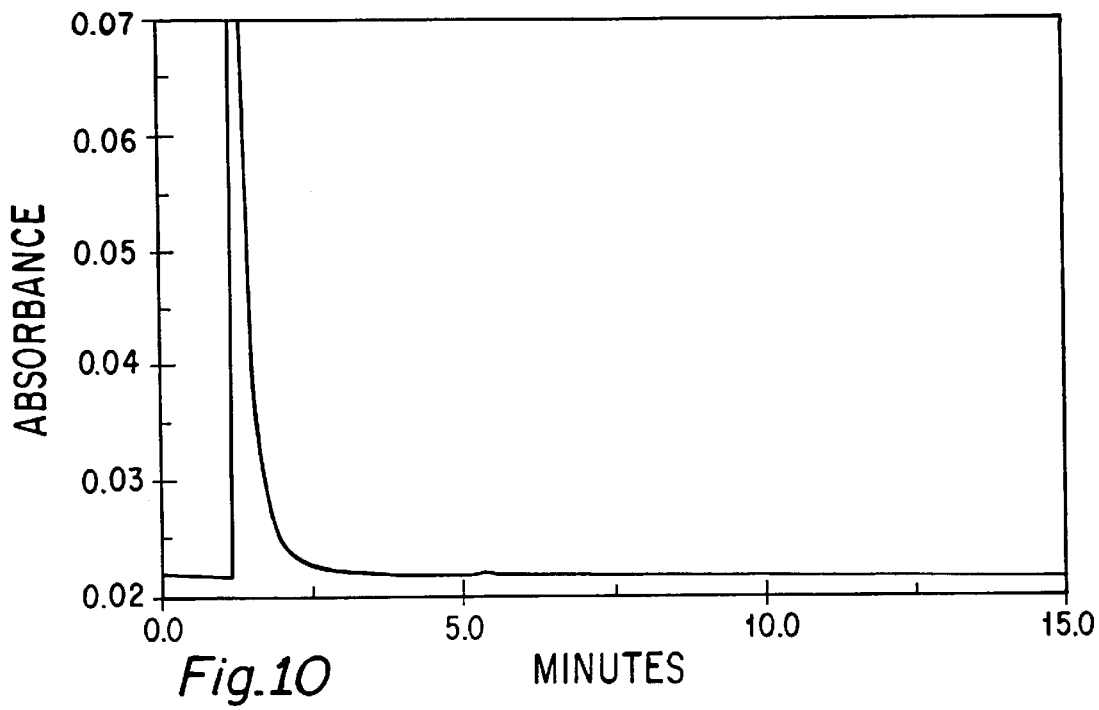
FIG. 10 shows the effect on the chromatography result shown in FIG. 9 when Cr(III) cations were added to the column before sample injection.
Figure 11:
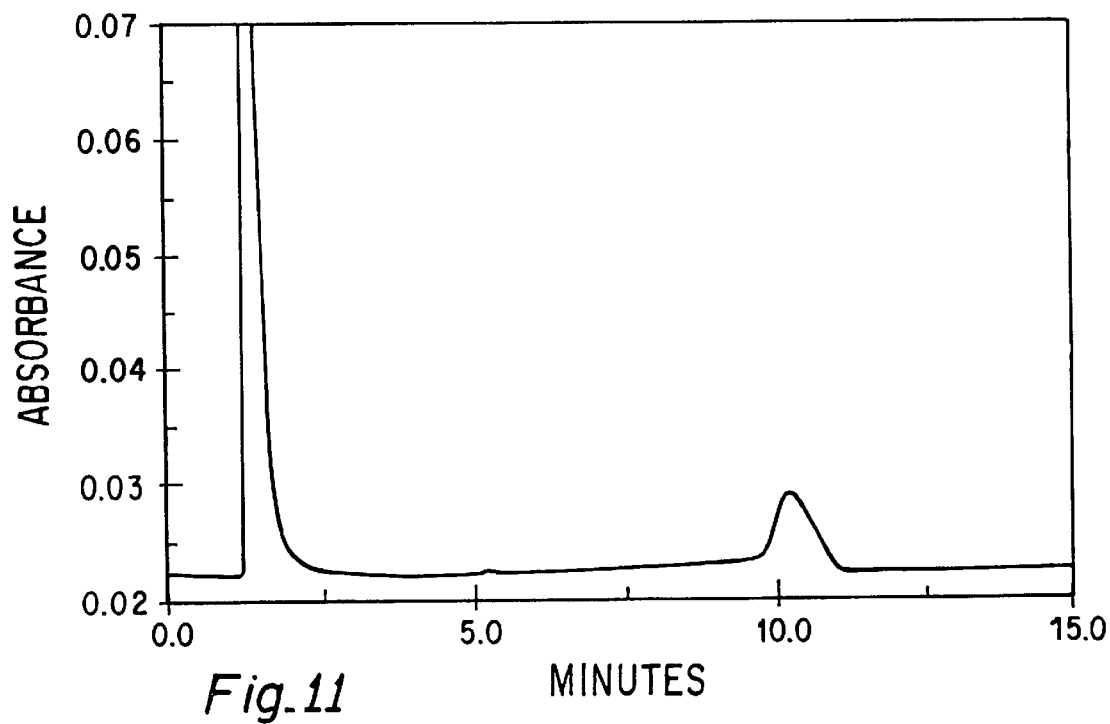
FIG. 11 shows the effect on the chromatography result of FIG. 10 when a Cr(III) contaminated column was treated with EDTA prior to sample injection.

Example 5 describes an sequence similar to Example 4, except that non-polar, wide pore silica separation media was used and washed with EDTA solution prior to sample injection. Once again, a sharp sample peak was obtained, as shown in FIG. 9, when the sample was injected onto a column containing cleaned separation media. Deliberate contamination of the separation media with Cr(III) resulted in complete loss of the sample peak, as shown in FIG. 10. Injection of EDTA solution to remove Cr(III), or other multivalent cations, followed by injection of the 500 base pair DNA sample, partially restored the sample peak as shown in FIG. 11.

Figure 12:
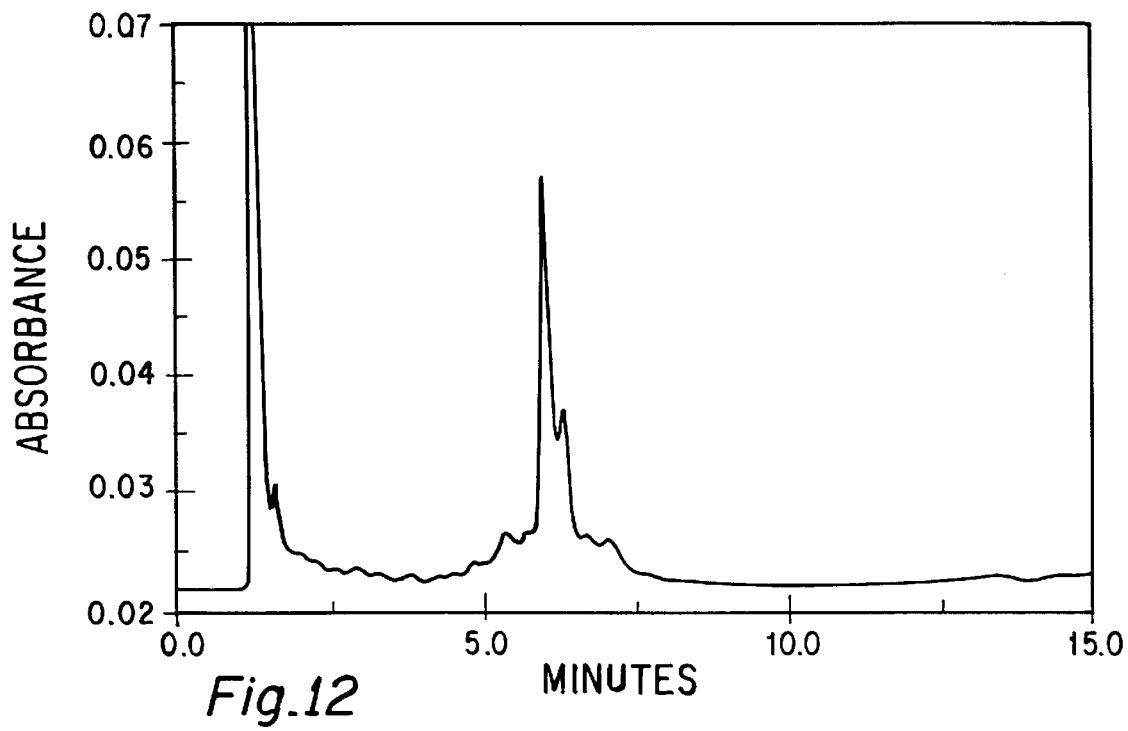
FIG. 12 shows the chromatography of a 20 mer single stranded DNA fragment standard (Seq 2A, CTGen, Milpitas, Calif.) on INERTSIL (MetaChem, Torrance, Calif.) C-18 non-polar, wide pore silica separation media which have been washed with EDTA to remove multivalent metal cations therefrom.
Figure 13:
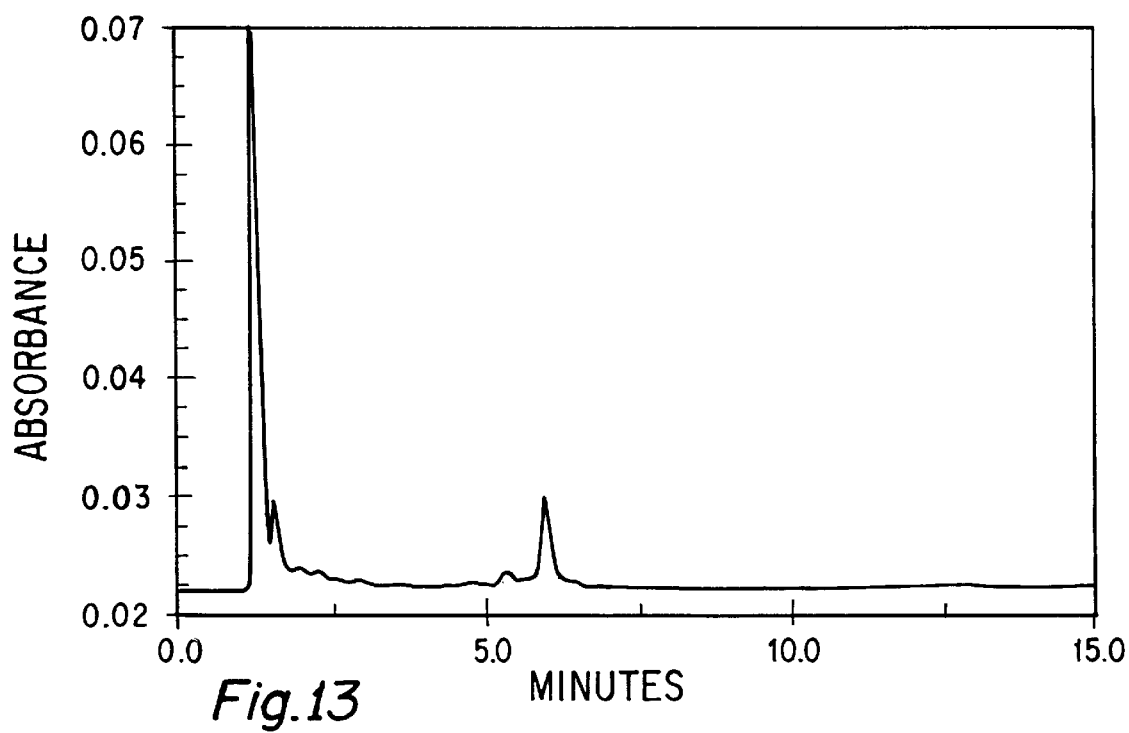
FIG. 13 shows the effect on the chromatography result shown in FIG. 12 when Cr(III) cations were added to the column before sample injection.

The deleterious effect of multivalent metal cations on the chromatographic separation of a 20 mer single stranded DNA standard is described in Example 6 and shown by the complete loss of resolution as seen in FIG. 13 (after deliberate Cr (III) contamination) compared to FIG. 12 (column cleaned with EDTA).

Figure 14:
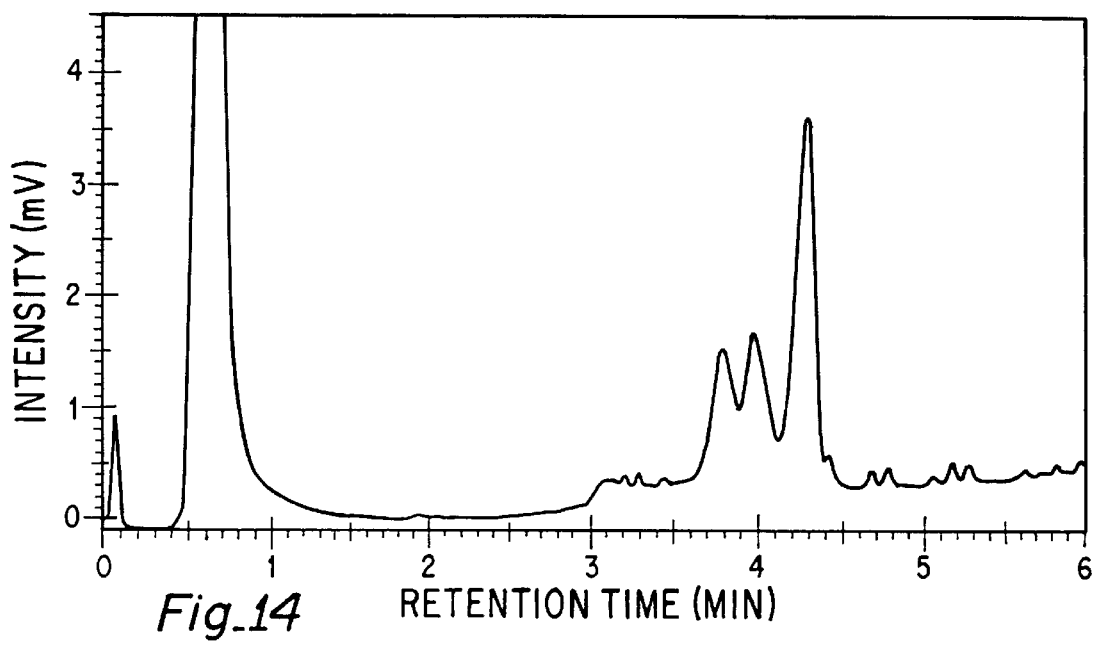
FIG. 14 shows the chromatographic separation at 56° C. of a 209 base pair DNA standard 4 component heteroduplex and homoduplex mixture on a freshly packed, untreated DNASep column (Transgenomic, Inc., San Jose, Calif.).
Figure 15:
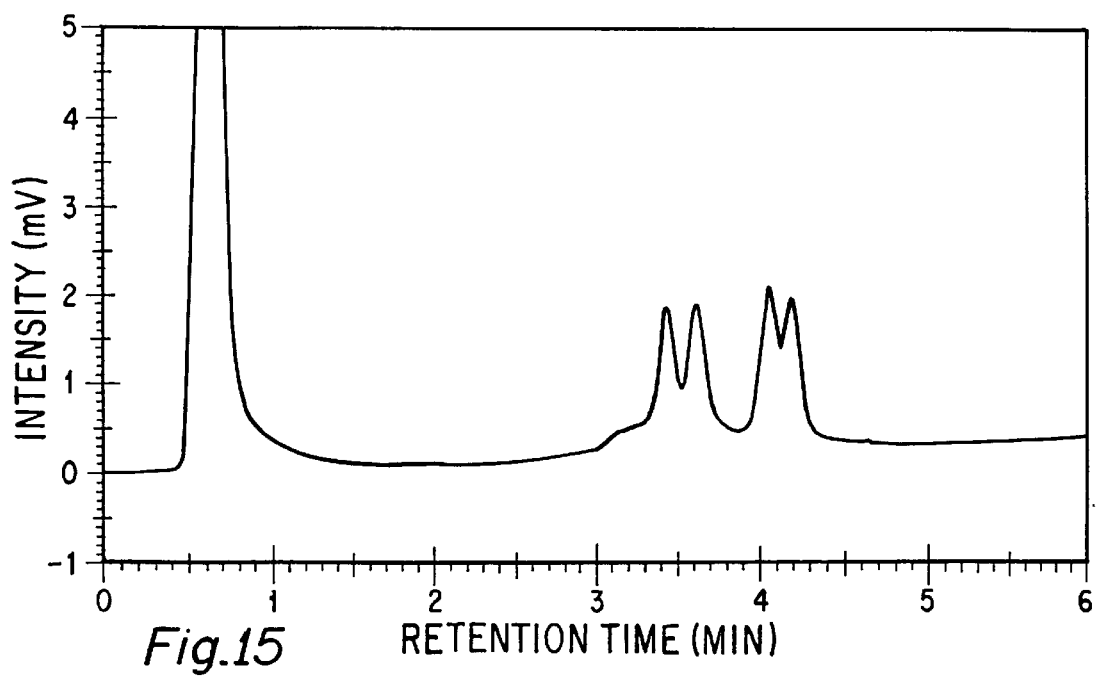
FIG. 15 shows the effect on the chromatography result shown in FIG. 14 when the column was treated with EDTA prior sample injection.

The deleterious effect of even trace levels of multivalent cations on demanding chromatographic separation is described in Example 7 and shown in FIGS. 14 and 15. A standard 4 component mixture of double stranded DNA consisting of two 209 base pair homoduplex fragments and two 209 base pair heteroduplex fragments were chromatographed at 56° C. as described in Example 6 on a freshly packed column DNASep column (Transgenomic, Inc., San Jose, Calif.). FIG. 14 shows only partial resolution of the 4 component mixture. However, when the column was treated with EDTA solution followed by re-injection and elution of the 4 component homoduplex/heteroduplex DNA mixture as described in Example 6, a clean separation of all 4 components was achieved, as seen in FIG. 15. This result clearly indicates that trace levels of multivalent cations were present in a freshly packed column, and that said cations interfered with the separation of double stranded DNA fragments.

The method of the invention can also be used to separate polynucleotide mixtures in a batch process useful for production and isolation of pure polynucleotide fragments of a plurality of selected sizes, on a small or large scale. The method of the invention comprises contacting a solution of a mixture of polynucleotide fragments containing a counterion agent with a multivalent metal cation capture resin, followed by applying said solution to non-polar, wide pore separation media. The separation media are held in a container. The container may be a column, a membrane, a container, or a web. The polynucleotide mixture is held on the separation media since the concentration of the organic component of the solvent in which the mixture is dissolved is not sufficient to release the polynucleotide fragments therefrom. The separation media are then contacted with a first eluting solvent and a counterion agent, said first eluting solvent having a concentration of the organic component sufficient to remove all polynucleotide fragments from the separation media which are smaller than the selected size. The eluting solvent is then separated from the separation media. The separation media are rinsed with the first eluting solvent to remove any remaining released polynucleotides. The separation media are then contacted with a second eluting solvent and counterion agent, said second eluting solvent having a concentration of the organic component sufficient to release the polynucleotide fragment having the selected size from the separation media. The second eluting solvent is separated from the separation media and the particles are rinsed with the second eluting solvent. This process can be repeated to release polynucleotide of any selected size which are present in the mixture.

Specific eluting solvent compositions required to elute polynucleotide fragments of any specific base pair length can be determined experimentally. For example, isolation of a 102 base pair fragment from the polynucleotide mixture may be desired, and said fragment may be eluted with 15.9% acetonitrile-water-0.1M triethylammonium acetate. In this example, the separation media holding the polynucleotide mixture may be contacted with 14.6% acetonitrile-water-0.1M triethylammonium acetate to remove reaction mixture reagents and additives, as well as all fragments having less than 102 base pairs. Increasing the acetonitrile concentration to 15.9% followed by contact of this eluting solvent with the non-polar, wide pore separation media will release the desired 102 base pair fragment, leaving larger fragments still attached to the separation media. The desired polynucleotide fragment dissolved in the eluting solvent is isolated by separating the eluting solvent from the separation media by filtering, decanting, centrifuging, or any other compatible liquid/solid separation technique. By using a step gradient of increasing acetonitrile concentration, larger particles may be removed in discreet base pair lengths from the separation media and isolated by repeating the procedure described hereinabove.

In a most preferred embodiment of the batch process of the invention, all the methods and procedures used to remove traces of multivalent cations from solvents and surfaces which contact process solution are identical to the methods and procedures described in separation method of the invention described hereinabove. All of process solution contract surfaces are of materials which do not release multivalent cations. Said materials are identical to those described in the separation method of the invention hereinabove.

The methods used to capture multivalent cations and prevent their presence in the batch process described hereinabove, are essential in order to achieve high resolution separations of polynucleotides, especially double stranded DNA, and also to greatly extend the useful life of the separation media.

The concepts, materials, systems and methods related to chromatographic separations on non-polar, wide pore separation media are well known and are described in detail in the following references: Chromatography Today, by Colin F. Poole and Salwa K. Pool, Elsevier (1991); Introduction to Modern Liquid Chromatography, L. R. Snyder and J. J. Kirland, J. Wiley and Sons, Inc. (1979). These references and references contained therein are incorporated in their entirety herein.

Non-polar, wide pore separation media and their use for the separation of polynucleotide mixtures are well known in the art and are commercially available, e.g., Hamilton HPLC Application Handbook, (1993), Hamilton Company, Inc., 4970 Energy Way, Reno, Nev. 89502. This, and references contained therein, are incorporated in their entirety herein. Another reference, which is incorporated in its entirety herein, describing polynucleotide separations on non-polar, wide pore reverse phase particles is Chromatography, 5th edition, Part B, edited by E. Heftmann, Elsevier (1992). Separation of tRNA and DNA fragment mixtures on non-polar, wide pore silica particles is described by R. Bischoff and L.W. McLaughlin, Analytical Biochemistry, 155, 526–533 (1985) and S. Eriksson, et. al., J. Chromatography, 359, 265–274 (1986). Regardless of the source or composition of the non-polar, wide pore separation media, precautions are taken to ensure that they are free of multivalent cation contaminants. For example, the separation media are washed with acid followed by methanol to ensure removal of residual multivalent cation contaminants.

Procedures described in the past tense in the examples below have been carried out in the laboratory. Procedures described in the present tense have not been carried out in the laboratory, and are constructively reduced to practice with the filing of this application.

EXAMPLE 1
Acid Wash Treatment To Remove Multivalent Metal Cation Contaminants The non-polar, wide pore reverse phase separation media were washed three times with tetrahydrofuran, then two times with methanol. The non-polar, wide pore separation media were then stirred for 12 hours with a mixture containing 100 mL of tetrahydrofuran and 100 mL of concentrated hydrochloric acid. Following this acid treatment, the non-polar, wide pore separation media were washed with tetrahydrofuran/water (1:1) until neutral (pH 7). The non-polar, wide pore separation media were then dried at 40° C. for 12 hours.

EXAMPLE 2
Standard Procedure for Demonstrating the Effects of Colloidal Iron on Non-polar, Wide pore Polymer Separation Media Non-polar, wide pore PRX-1 separation media (Sarasep, Inc. San Jose, Calif.) of polystyrene/divinylbenzene polymer having a pore size of 50–200 Angstroms (average pore size is 80 Angstroms) and a bead diameter of 5 microns are washed as described in Example 1 and packed in a 4.6×50 mm HPLC column. A sample (5 $\mu$L, 20 ng) of 80 base pair DNA standard solution from purified pUC18 DNA Hae III restriction enzyme digest (Sigma-Aldrich, D6293) is injected onto the column. The chromatography is conducted under the following conditions: Eluting solvent A: 0.1 M Triethylammonium acetate (TEAA), pH 7.2; Eluting solvent B: 0.1 M TEAA, 25% acetonitrile; Gradient:

| Time (min) | % A | % B |
|---|---|---|
| 0.0 | 65 | 35 |
| 3.0 | 45 | 55 |
| 10.0 | 35 | 65 |
| 14.0 | 0 | 100 |
| 16.0 | 65 | 35 |

The flow rate is 0.75 mL/min, UV detection at 260 nm, column temp. 51° C. A peak for the 80 base pair DNA fragment is obtained. Some columns, depending on the packing volume and packing polarity, may require longer time for elution of some changes in the driving solvent concentration.

A 0.05M aqueous solution of $Fe(Cl)_3$ is prepared and allowed to stand at ambient temperature for four hours. A 100 $\mu$L sample of the resulting colloidal iron suspension is injected onto the column and allowed to stand for five minutes. Subsequent injection Of 5 $\mu$L of the above described 80 base pair DNA standard solution followed by the identical gradient elution conditions described above, shows a complete absence of any peak.

EXAMPLE 3
Standard Procedure for Demonstrating the Effects of Colloidal Iron on Non-polar, Wide pore Silica Separation Media INERTSIL (MetaChem, Torrance, Calif.), a 5 $\mu$m C-18 non-polar, wide pore separation medium having 200 Angstrom pores was packed in a 4.6×50 mm HPLC column and cleaned with 5 injections of 0.1 M $Na_4EDTA$. A 80 base pair DNA standard (5 $\mu$L) is injected and eluted as described in Example 2. A peak for the 80 base pair DNA standard is obtained.

An injection of the colloidal iron suspension is made as described in Example 3. Subsequent injection of the 80 base pair DNA standard and elution as described in Example 3 shows a complete absence of any peak.

EXAMPLE 4
Standard Procedure for Demonstrating the Effects of Chromium(III) On The Separation of Double Stranded DNA Using Non-polar, Wide Pore Polymer Separation Media Non-polar, wide pore PRX-1 separation media (Sarasep, Inc., San Jose, Calif.) of polystyrene/divinylbenzene polymer having a 5 micron diameter and a pore size of 50–200 Angstroms (80 Angstrom average pore size) was washed as described in Example 1 and packed in 4.6×50 mm HPLC column. A sample (5 $\mu$L, 20 ng) of 500 base pair DNA standard solution from GeneAmp$^R$ Lambda Control Reagent, N808-0008, (Perkin Elmer, Foster City, CA) was injected onto the column. The chromatography was conducted under the following conditions: eluting solvent A; 0.1M triethylammonium acetate (TEAA), pH 7.2; eluting solvent B; 0.1M TEAA, 25% acetonitrile gradient:

| Time (min) | % A | % B |
|---|---|---|
| 0.0 | 60 | 40 |
| 14 | 0 | 100 |
| 17 | 60 | 40 |

The flow rate was 0.60 mL/min, UV detection at 260 nm, column temperature 50° C. A peak for the 500 base pair DNA fragment was obtained, as shown in FIG. 6.

A 520 ppm aqueous solution of Cr(III) was prepared from $Cr_3(SO_4)_2 \cdot 12H_2O$ and injected onto the column. The 17 min. solvent gradient was flowed through the column. Injection of 5 μL of the 500 base pair DNA standard onto the column and elution as described above, showed a complete absence of any peak (FIG. 7).

A subsequent column cleanup with 3 injections, 10 μL each, of 0.1M $Na_4EDTA$ was followed by equilibration to a constant baseline. A re-injection of 5 μL of the 500 base pair DNA standard showed a reappearance of the a peak (FIG. 8) having an area of about 50% of the original injection (FIG. 6).

EXAMPLE 5
Standard Procedure for Demonstrating the Effects of Chromium(III)) On The Separation of Double Stranded DNA Using Non-polar, Wide Pore Silica Separation Media INERTSIL (MetaChem, Torrance, Calif.) 5 micron C-18 non-polar, wide pore (150 Angstrom pores) separation media was packed into a 4.6×50 mm HPLC column and cleaned with 5 injections of 0.1M $Na_4EDTA$. A 500 base pair DNA standard was injected onto the column and eluted as described in Example. 4. A peak for the 500 bas pair standard is shown in FIG. 9.

Injection of the Cr(III) solution as described in Example 4 followed by elution as described in Example 4, showed a complete absence of a peak as shown in FIG. 10.

Three 10 mL injections of $Na_4EDTA$ as described in Example 4 follwed by reinjection of the 500 base pair DNA standard and elution as described in Example 4, showed a peak (FIG. 11 )corresponding to the 500 base pair DNA standard.

EXAMPLE 6
The Effect of Chromium(III) on the Separation of Single Stranded DNA Using Non-polar, Wide Pore Silica Separation Media The column described in Example 5 was cleaned with $Na_4EDTA$ as described in Example 5 and equilibrated with 60% A eluting solvent to a constant bse line. A 20 mer, single stranded DNA standard (Seq2A purchased from CTGen, Milpitas, Calif.) was injected onto the column and eluted with the gradient protocol of Example 4. FIG. 12 shows a major peak corresponding to the 20 mer standard and some well resolved impurity peaks.

A single 5 mL injection of the Cr(III) solution described in Example 4 was followed by re-injection of the 20 mer standard and elution using the gradient protocol of Example 4. The results seen in FIG. 13 show a greatly diminished peak corresponding to the 20 mer, and essentially no resolution of the impurities.

This example clearly show that metal contamination has a negative effect on the chromatography of single stranded DNA but not to the same extent as it has on double stranded DNA.

An additional injection of 5 μL onto the column followed by another injection of the 20 mer standard as described above, did result in complete elimination of the 20 mer peak. However, after 10 injections of 0.1M $Na_4EDTA$ to remove metal contamination, as described above, followed by another injection of the 20 mer standard, did restore the peak corresponding to the 20 mer standard. However, the peak shape was distorted and broad.

EXAMPLE 7
The Effect of Metal Contamination on the Separation of Heteroduplexes and Homoduplexes A freshly packed DNASep column (Transgenomic, Inc., San Jose, Calif.) was equilibrated with eluting solvent 50% A. A mixture of DNA 209 base pair standard fragments (Transgenomic, Inc., San Jose, Calif., Cat. No. 560012) consisting of 2 heteroduplex DNA fragments and 2 homoduplex DNA fragments was injected (5 μL) onto the column. The mixture was eluted at a flow rate of 0.9 mL/min using the following gradient program:

| Time (min) | % A | % B |
|---|---|---|
| 0.0 | 50 | 5 |
| 05 | 47 | 53 |
| 4.0 | 40 | 60 |
| 5.5 | 0 | 100 |
| 6.5 | 50 | 50 |
| 8.5 | 50 | 50 |

When the chromatography was run at 50° C. a normal size based separation was observed, i.e., a single peak of unresolved hetroduplex and homoduplex 209 base pair fragments was observed.

FIG. 14 shows the results of a chromatography run at 56° C., on a newly packed column. Three peaks are seen. The low retention time pair corresponds to the two heteroduplexes. The large higher retention time peak corresponds to the unresolved homoduplex peaks. The lack of complete separation of all four fragments indicated that the column, though freshly packed, contained multivalent metal cation contaminants.

Column cleanup with 5, 10 μL injections of 0.1M $Na_4EDTA$ was followed by washing with 25% actonitrile, 5% acetic acid, and equilibration to constant base line with eluting solvent 50% A. Injection of the 209 fragment standard homoduplex/heteroduplex mixture and elution with the gradient protocol described above, gave complete separation of the mixture into four peaks, i.e., two homoduplex and 2 heteroduplex peaks as depicted in FIG. 15.

The results described in this example indicate that multivalent metal cation contamination is more critical at higher column temperatures, especially as related to the difficult separation of homoduplex and heteroduplex fragments of identical base pair length.

What is claimed is:
1. A batch process for separating polynucleotide fragments having a selected size from a mixture of polynucleotide fragments including fragments of said selected size comprising
   a) applying a solution of said polynucleotide fragments and a counterion agent to non-polar separation media having a non-polar surface, wherein said separation media have a pore size greater than 30 Angstroms and an average diameter of 1–100 microns;
   b) contacting the separation media with a first eluting solvent and counterion agent, the first eluting solvent having a concentration of organic component sufficient to release from the separation media all polynucleotide fragments having a size smaller than the selected size and removing the first eluting solvent from the separation media; and c) contacting the separation media with a second eluting solvent having a concentration of organic component sufficient to release from the separation media the polynucleotide fragments having the selected size and removing the second eluting solvent from the separation media;

wherein surfaces which are contacted by the solution of polynucleotide fragments and the eluting solvent are material which does not trap or release multivalent metal cations therefrom.

2. A batch process of claim 1 wherein the separation media are rinsed with fresh first eluting solvent following step b) to remove residual released polynucleotide fragments therefrom.

3. A batch process of claim 1 wherein the separation media are rinsed with fresh second eluting solvent following step c) to remove residual released polynucleotide fragments of selected size therefrom.

4. A batch process of claim 1 wherein the polynucleotide mixture is double stranded or single stranded.

5. A batch process of claim 1 wherein the solution of polynucleotide mixture and eluting solvent have been contacted with a multivalent cation capture resin before contacting the separation media.

6. A batch process of claim 5 wherein said separation media have been treated to remove residual traces of multivalent cations therefrom.

7. A batch process of claim 6 wherein the solution of polynucleotide mixture and eluting solvent have been contacted with a multivalent cation capture resin before contacting the separation media.

8. A batch process of claim 7 wherein the separation media are contained in a column, a web, a membrane, or container.

9. A batch process of claim 8 wherein said separation media are organic polymer or inorganic substrates selected from the group consisting of inorganic substrates, silica, zirconium, and alumina.

10. A batch process of claim 9 wherein the non-polar surface is an organic polymer supported on the inorganic substrate.

11. A batch process of claim 9 wherein the non-polar surface includes long chain hydrocarbons having from 8–24 carbons bonded the inorganic substrate.

12. A batch process of claim 11 wherein any residual polar groups of the inorganic substrate have been end capped with trimethylsilyl chloride or hexamethyidisilazane.

13. A batch process of claim 8, wherein the surfaces contacted by the solution of polynucleotide fragments and eluting solvent are comprised of material selected from the group consisting of titanium, coated stainless steel, and organic polymer, or combinations thereof.

14. A batch process of claim 13 wherein traces of residual multivalent metal cations have been removed from said surfaces by treating said surfaces with a solution comprising aqueous acid and chelating agent.

15. A batch process of claim 13 wherein organic contaminants have been removed from said surfaces.

16. A batch process of claim 7 wherein said solution of polynucleotide mixture and eluting solvent contain a chelating agent whereby any trace of multivalent metal cations in the solution are captured.

17. A batch process of claim 1 wherein the eluting solvent has been treated to remove oxygen therefrom.

* * * * *